US007267975B2

(12) United States Patent
Strobel et al.

(10) Patent No.: US 7,267,975 B2
(45) Date of Patent: Sep. 11, 2007

(54) METHODS AND COMPOSITIONS RELATING TO INSECT REPELLENTS FROM A NOVEL ENDOPHYTIC FUNGUS

(75) Inventors: Gary Strobel, Bozeman, MT (US); Bryn Daisy, Anchorage, AK (US)

(73) Assignee: Montana State University, Bozeman, MT (US)

( * ) Notice: Subject to any disclaimer, the term of this patent is extended or adjusted under 35 U.S.C. 154(b) by 234 days.

(21) Appl. No.: 10/687,546

(22) Filed: Oct. 15, 2003

(65) Prior Publication Data
US 2004/0185031 A1    Sep. 23, 2004

Related U.S. Application Data

(60) Provisional application No. 60/418,396, filed on Oct. 15, 2002.

(51) Int. Cl.
*A01N 25/00* (2006.01)
*A01N 63/00* (2006.01)
*A01N 63/04* (2006.01)
*A01N 65/00* (2006.01)
*C12N 1/00* (2006.01)
*C12P 1/02* (2006.01)
*C12P 7/00* (2006.01)
*C07C 409/44* (2006.01)

(52) U.S. Cl. ............... 435/254.1; 424/93.5; 424/405; 435/132; 435/171; 435/911

(58) Field of Classification Search ............ None
See application file for complete search history.

(56) References Cited

U.S. PATENT DOCUMENTS

| | | | |
|---|---|---|---|
| 4,954,497 A | 9/1990 | Kamikado et al. | |
| 5,270,340 A | 12/1993 | Kunisch et al. | |
| 5,612,338 A | 3/1997 | Trah | |
| 6,310,005 B1 | 10/2001 | Assmann et al. | |
| 6,911,338 B2 * | 6/2005 | Strobel et al. | ............ 435/254.1 |

OTHER PUBLICATIONS

Agency for Toxic Substances and Disease Registry. (1995). World-Wide-Web Page at http://www.atsdr.cdc.gov/tfacts67.html (Modified: Sep. 2003).
Azevedo, J. L., et al. "Endophytic microorganisms: a review on insect control and recent advances on tropical plants," *Electronic Journal of Biotechnology*, 3(1):40-65 (Apr. 15, 2000).
Azuma, H., et al. "Naphthalene- constituent of magnolia flowers," *Phytochemistry*, 42(4):999-1004 (1996).
Bayman, P. et al. "Distribution and dispersal of *Xylaria* endophytes in two tree species in Puerto Rico," *Mycological Research*, 102(8):944-948 (1997).
Bolton, D. M., et al., in the Merck Index, 8th edn ed. (Stecher, P.G. Windholz, M., and Leahy, D. S.) 713 (Merck, Rathway, New Jersey, (1968).
Bruns, T.D., et al. "Fungal molecular systematics," *Annu. Rev. Ecol. Syst.*, 22:525-564 (1991).

Chen, J., et al. "Termites fumigate their nests with naphthalene," *Nature*. 392:558-559 (Apr. 1998).
Daisy, B. H. et al. "*Muscodor vitigenus*, anam. sp. nov. an endophyte from *Paullinia paullinioides*," *Mycotaxon* 84:39-50. (2002).
Daisy, B. et al "Napthalene, an insect repellent, is produced by *Muscodor vitigenus*, a novel endopythic fungus", *Microbiology* (2002), 148, 3737-3747.
Guarro, J. et al. "Developments in Fungal Taxonomy," *Clin Microbiol Rev*. 12(3):454-500, (Jul. 1999).
Hawksworth, D. C. et al. "Where are the undescribed fungi?" *Phytopath* 87(9):888-891 (1987).
Heath, R. R., et al. "Development and evaluation of systems to collect volatile semiochemicals from insects and plants using a charcoal-infused medium for air purification," *Journal of Chemical Ecology*. 18(7):1209-1226 (1992).
Mitchell, J. I., et al. "Sequence or Structure? A Short Review on the Application of Nucleic Acid Sequence Information to Fungal Taxonomy," *Mycologist*. (1995).
Morrill, W. L., et al. "Trap strip and field border modification for management of the wheat stem sawfly: (*Hymenoptera cephidae*)," *Journal of Entomological Science*. 36(1):34-45 (2001).
Pinkerton, F., et al. "Serinol as an activator of toxin production in attenuated cultures of *J. sacchari*," *Proc. Natl. Aca. Sci*, (USA) 73(11):4007-4011 (Nov. 1976).
Sambrook, J., et al. "Molecular Cloning: a Laboratory Manual." 2nd Edition. Edited by Ford, N., Nolan, C., and Ferguson, M., Cold Harbor Laboratory Press, New York. (1989).
Schutz, B., "Endophytic fungi: a source of novel biologically active secondary metabolites." British Mycological Society, International Symposium Proceedings, Bioactive Fungal Metabolites—Impact and Exploitation, University of Wales, *Mycol. Res.* 106(9):996-1004 (Apr. 2001).
Stone, J. K., et al. "An Overview of Endophytic Microbes: Endophytism Defined" in Microbial Endophytes ed. (Bacon, C.W. and White J. F.), Marcel Dekker, Inc, New York. (2000).
Strobel, G. A., et al. "*Pestalotiopsis jesterii* sp. nov. an endophyte from *Fragraea bodenii*, a common plant in the southern highlands of Papua New Guinea," *Mycotaxon* 76:257-266. (2000).
Strobel, G. A., et al. "Taxol from *Pestalotiopsis microspora*, an endophytic fungus of *Taxus wallachiana*," *Microbiology* 142:435-40 (1996).

(Continued)

*Primary Examiner*—Irene Marx
*Assistant Examiner*—Deborah K. Ware
(74) *Attorney, Agent, or Firm*—Klarquist Sparkman, LLP

(57) ABSTRACT

The present invention relates to the discovery of a novel endophytic fungus, *Muscodor vitigenus*, from the liana, *Paullinia paullinioides*. This fungus produces naphthalene under certain cultural conditions that has chromatographic and mass spectral properties that are identical to authentic naphthalene. In a preferred embodiment, the naphthalene in the gas phase of *M. vitigenus* is useful in the repellency of unwanted insect pests. The unique biological activity of the novel endophyte suggests a wide range of potential practical applications, particularly in the area of insect repellents, insecticides, antimicrobials, anthelmintics and vermicides.

11 Claims, 4 Drawing Sheets

OTHER PUBLICATIONS

Strobel, G. A., et al. "Volatile antimicrobials form *Muscodor albus*, a novel endophytic fungus." *Microbiology* 147:2943-2950, (2001).

Taylor, J. W., et al. The Evolution of asexual fungi: Reproduction, Speciation, and Classification. *Annu. Rev. Phytopathol* 37:197-246 (Sep. 1999).

Weiland, J.J., http://www.fgsc.net/fgn44/weiland.html, Northern Crop Science Laboratory, Sugarbeet and Potato Research Unit, Fargo, N.D. USA (Published: 1997).

White, T.J. et al. "Amplification of direct sequencing of fungal ribosomal RNA genes for phylogenetics." In PCR Protocols: A Guide to Methods and Applications. Edited by Innis, M.A., Gelfand, D. H., Snisky J.J., and White, T. J., Academic Press, Inc., California, (1990).

Worapong, et al. "*Muscodor albus anam. gen. et sp. nov.*, an endophyte from *Cinnamomum zeylanicum*," *Mycotaxon* 79:67-79 (2001).

Worapong, et al. "*Muscodor roseus anam. sp. nov.*, an endophyte from *Grevillea pteridifolia*," *Mycotaxon* 81:463-475 (2002).

Zadoks, J. C., et al. "A decimal code for the growth stages of cereals" *Weed Research* 14:415-421 (1974).

* cited by examiner

METHODS AND COMPOSITIONS RELATING TO INSECT REPELLENTS FROM A NOVEL ENDOPHYTIC FUNGUS

STATEMENT REGARDING RESEARCH & DEVELOPMENT

This research was funded under NSF Research Grant No. 0114469.

CROSS-REFERENCE TO RELATED APPLICATION

This application claims benefit of priority to U.S. Ser. No. 60/418,396, filed Oct. 15, 2002, under 35 U.S.C. §119 now abandoned.

The entire disclosure of the prior application is considered to be part of the disclosure of the instant application and is hereby incorporated by reference therein.

FIELD OF THE INVENTION

The present invention relates to the discovery of a novel endophytic fungus, *Muscodor vitigenus*, from the liana, *Paullinia paullinioides*. This fungus produces naphthalene under certain cultural conditions that has chromatographic and mass spectral properties that are identical to authentic naphthalene. In a preferred embodiment, the naphthalene in the gas phase of *M. vitigenus* is useful in the repellency of unwanted insect pests. The unique biological activity of the novel endophyte suggests a wide range of potential practical applications, particularly in the area of insect repellents, insecticides, antimicrobials, anthelmintics and vermicides.

BACKGROUND OF THE INVENTION

It has been estimated that there may be as many as 1 million different fungal species on our planet (Hawksworth, D. C. and A. Y. Rossman, A. Y., 1987. "Where are the undescribed fungi?", Phytopath. 87, 888-891). In the past century, many of the 0.1 million fungi that have been described have been those associated with various higher organisms as either parasites or saprophytes on dead and dying biological materials. Thus, the question, where are the remaining 0.9 million fungi? It turns out that microorganisms seem to occupy virtually every living and non-living niche on earth. This includes those in the thermal vents, in deep rock sediments, and in desert as well as marine environments.

In the past few decades, plant scientists have begun to realize that plants may be serving as a reservoir of untold numbers of organisms known as endophytes (Bacon, C. W., and White, J. F. 2000. Microbial Endophytes. Marcel Deker Inc., N.Y.). Endophytic fungi and bacteria are those organisms living within the tissues of host plants. By definition, these microorganisms (mostly fungi and bacteria) live in the intercellular spaces of plant tissues. Typically, endophytes coexist with their hosts without any pathogenic symptoms. These organisms have proven to be an unusually rich source of novel bioactive natural products.

Some of these endophytes may be producing bioactive substances that, in some way may be involved in the host—endophyte relationship. As a direct result of the role that these secondary metabolites may play in nature, they may ultimately be shown to have applicability in medicine, agriculture and industry. We are now witnessing the beginning a worldwide scientific effort to isolate endophytes and study their natural products. While there are many epiphytic microorganisms associated with plants, the endophytic associations may be more complex since living host tissues are involved. This may be the case since closer biological associations may have developed between these organisms in their respective hosts than the epiphytes or soil related organisms. Hence, the result of this may be the production of a greater number and diversity of classes of biological derived molecules possessing a range of biological activities. In fact, a recent comprehensive study has indicated that 51% of biologically active substances isolated from endophytic fungi were previously unknown (Schutz, B. 2001. British Mycological Society, International Symposium Proceedings, Bioactive Fungal Metabolites-Impact and Exploitation. University of Wales, April). This compares with only 38% novel substances from soil microflora.

One of the least studied biochemical-chemical systems in nature is the relationship existing between microorganisms and their plant hosts. For instance, it does appear that all higher plants are hosts to one or more endophytic microbes. These microbes include the fungi, bacteria and actinomycetes. They reside in the tissues beneath the epidermal cell layers. It is well understood that endophytic infections are at least inconspicuous (Bacon, C. W., and White, J. F. 2000. Microbial Endophytes. Marcel Deker Inc., N.Y.). And as a result, the host tissues are transiently symptomless and the colonization of the tissues is internal to the surface of the plant. The exact physical relationship of the endophyte to the plant has, in most cases remained obscure, because it is extremely difficult, by electron microscopic techniques, to find an endophyte within plant tissues. Conceivably, the microbes live within the intercellular spaces of the tissues and it also seems likely that penetration of living cells may occur but not easy to observe. The relationship that any given endophyte establishes with the plant varies from symbiotic to that bordering on pathogenic.

It also turns out that these relationships may have begun to evolve from the time that higher plants first appeared on the earth hundreds of millions years ago. Evidence of plant associated microbes has been discovered in the fossilized tissues of stems and leaves (Bacon, C. W., and White, J. F. 2000. Microbial Endophytes. Marcel Deker Inc., N.Y.). As a result of these long held associations, it is possible to imagine that some of these endophytic microbes may have devised genetic systems allowing for the transfer of information between themselves and the higher plant and visa versa. Obviously, this would permit a more rapid and reliable mechanism of the endophyte to deal with ever changing environmental conditions and perhaps allow for more compatibility with the plant host. In addition, independent evolution of the endophytic microbes may have allowed them to better adapt to a plant host and perhaps develop to a point where they could contribute to their relationship to their host plant by carrying out such functions as protection from pathogens, insects, and other grazing animals. Or in still another case, it is possible to imagine that certain products from the endophyte may protect the plant from the harmful effects of irradiation, oxidation, and other events that occur as a natural consequence on living on this earth.

Recently, we described two novel endophytic fungi, *Muscodor albus* from *Cinnamomum zeylanicum* from Honduras (Worapong et al., 2001), and *M. roseus* from two monsoonal rainforest trees in Northern Australia (Worapong et al., 2002). These endophytes produce a mixture of volatile antimicrobials that effectively inhibit and kill a wide spectrum of plant-associated fungi and bacteria (Strobel et al., 2001). On the other hand, the gases of *M. albus* did not kill fungi that were related to it, some of which were producers of other lethal gas mixtures (Worapong et al., 2001 and Worapong et al., 2002).

Accordingly, it is an object of the present invention to provide additional *Muscodor* species that have biological activity.

SUMMARY OF THE INVENTION

In accordance with the above objects, the present invention provides isolated cultures of *Muscodor vitigenus* including variants thereof. The compositions of the invention can include isolated cultures and carriers, particularly agriculturally acceptable carriers, including soil.

In a further aspect, the invention provides methods of repelling an insect from a first composition comprising contacting said first composition with a second composition comprising an isolated culture of *M. vitigenus*. The first composition can be a plant, a work surface, an industrial surface, a home surface, etc., including plant parts.

DETAILED DESCRIPTION OF PREFERRED EMBODIMENTS

Figure 3:
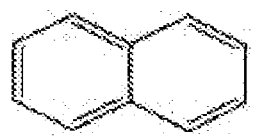
FIG. 3. The structure of naphthalene
Figure 4:
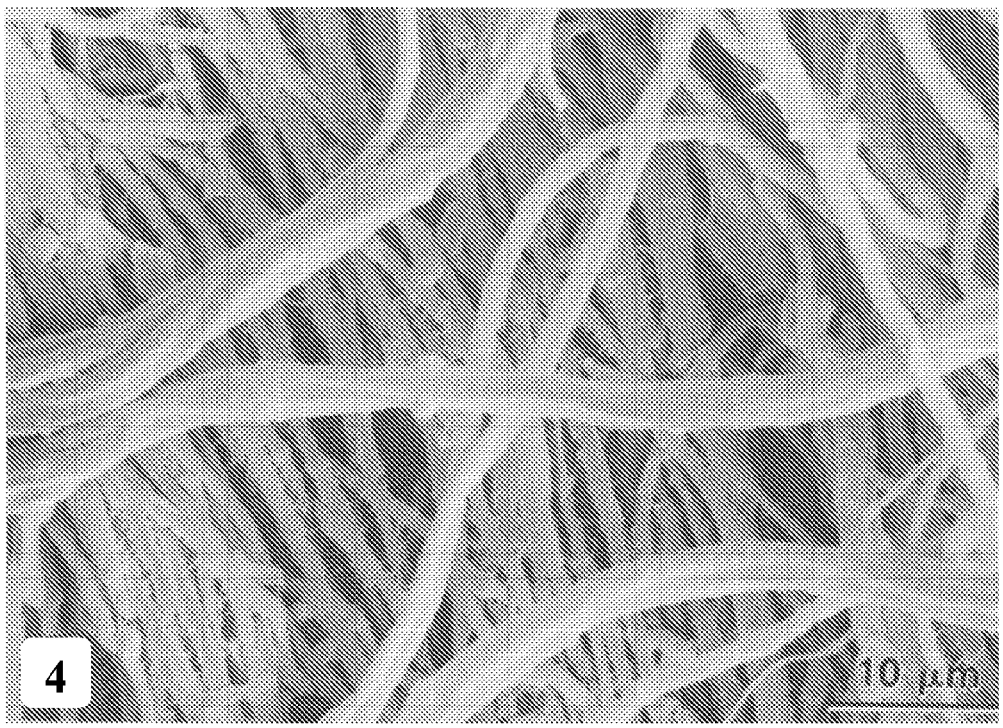
FIG. 4. Scanning electron micrograph of hyphae and mycelium of *M. vitigenus* growing on PDA. Please note the branching of individual hyphae from rope-like strands.
Figure 5:
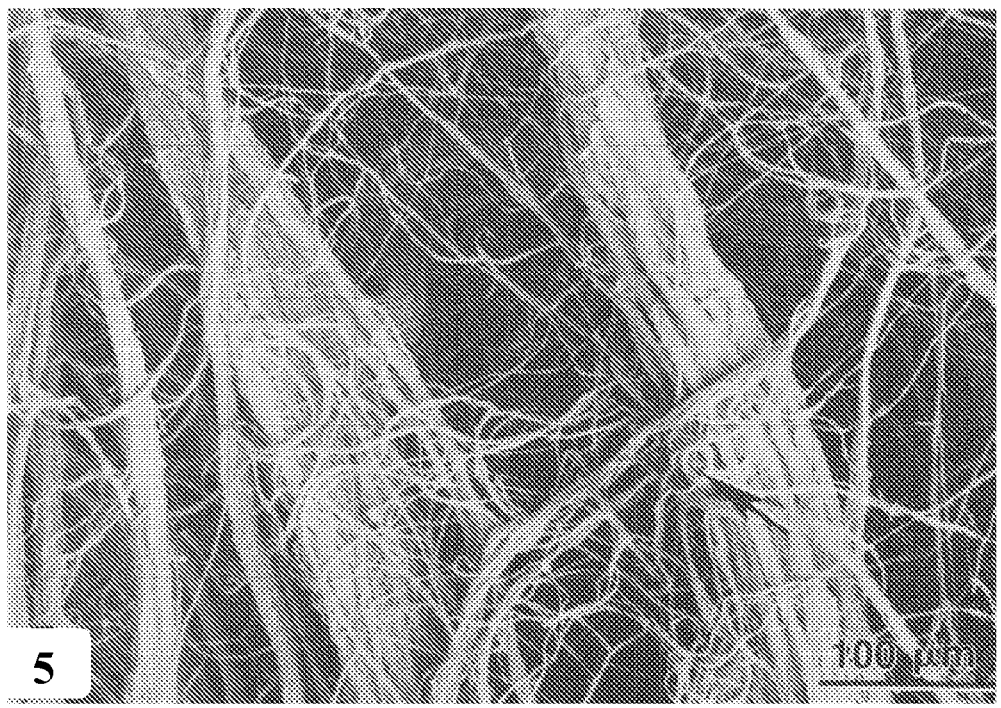
FIG. 5. Scanning electron micrograph showing the twisted cable-like strands of mycelium. Please note the example of a nearly perfect coil structure (arrow).
Figure 6:
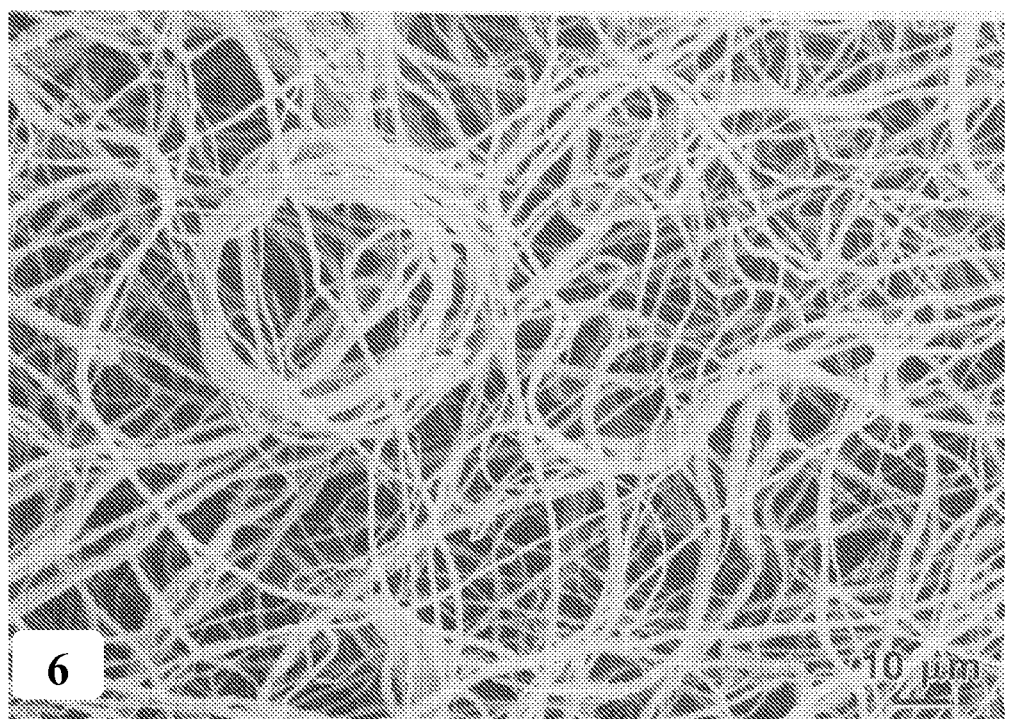
FIG. 6. Scanning electron micrograph of a coil structure of hyphae of *M. vitigenus*.
Figure 7:
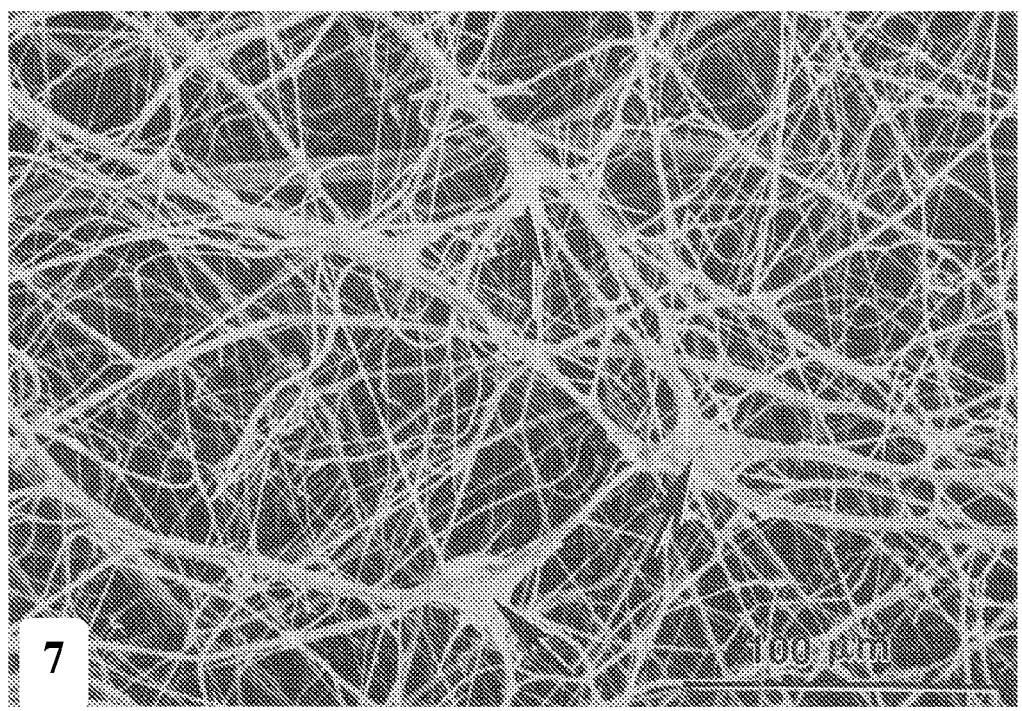
FIG. 7. Scanning electron micrograph of hyphae appearing to have secreted a matrix-like substance (arrows).

The present invention is directed to biologically pure cultures of a novel *Muscodor* species, *M. vitigenus*, the first endophyte and fungus known to produce naphthalene as a secondary metabolite. This unique endophytic fungus produces naphthalene in quantities that are great enough to cause modifications in insect behavior. Naphthalene as a product from biological sources is exceedingly rare. Thus, the observation that naphthalene is produced by the endophytic fungus—*M. vitigenus* is not only unique to this group of *Muscodor* spp. but to all endophytic fungi as well (FIG. 3). Its role in the endophyte maybe related to the ability of naphthalene to inhibit some types of fungal proliferation (Chen et al., 1998), thus providing *M. vitigenus* the capability to ward off competitors in its natural environment, not only assisting the host, but its own survival. Generally, in commerce, naphthalene is used as an antimicrobial, an insecticide, an insect repellant, an anthelmintic, and a vermicide (Bolton and Eaton, 1968). Naturally, naphthalene is found in fossil fuels and produced by the burning of coal, oil, and wood (ATSDR, 1995). Only recently has naphthalene been found as a constituent of other natural-biological systems, having been reported from Magnolia flowers as well as in the nest material of Formosan subterranean termites; it has been suggested that the presence of the chemical in both of these places may function as protection from insects (Azuma et al., 1996; Chen et al., 1998).

Accordingly, the present invention provides biologically pure cultures of the *M. VITIGENUS* isolate designated 2116. By "biologically pure" or "isolated" or grammatical equivalents herein is understood in the art to mean a culture fluid, plate, paper, etc. that contains a single type of organism. In general, as applied to the current invention, tissue fragments from *P. paullinoidides* are placed in either culture fluid or agar (e.g. mycological agar) until fungal growth occurs, as is outlined in the examples. Fungal hyphae from the fungal growth is grown and serially transferred until a culture in pure form is obtained, as measured by observation (e.g. morphological and/or genetic unity).

The *M. vitigenus* isolate 2116 can be identified and characterized in a variety of ways, most notably that cultures of *M. vitigenus* 2116 produce naphthalene, including naphthalene derivatives, as described herein, in addition to traces of other volatiles as described herein. Thus, MV can be identified as a *Muscodor* species, using well known techniques, generally by classification with the *Muscodor* genus on the basis of the relatedness of the 18S rDNA sequence to previously identified members of the *Muscodor* genus, as well as similarity of its hyphae to other *Muscodor* species (as outlined in the Examples and shown in FIGS. 4-7).

In addition, *M. vitigenus* 2116 has been deposited in the Montana State University living culture collection and designated as such. *M. vitigenus* 2116 has also been deposited in the Centraalbureau voor Schimmelcultures (P.O. Box 85167, 3508 AD UTRECHT, The Netherlands) depository on July 31, 2006 and designated by Accession No. CBS 120164. Moreover, *M. vitigenus* 2116 has been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposit represents a substantiallypure culture of the deposited strain. The deposit is available as required under the terms of the Budapest Treaty. All restrictions on the availability to the public of the material so deposited will be irrevocably removed upon the granting of a patent. However, it should be understood that the availability of a deposit does not constitute a license to practice the subject invention in derogation of patent rights granted by governmental action. Further, certain genetic sequences of the organism have been elucidated, namely its ITS, 5.8S and ITS2 sequences deposited in GenBanik under accession numbers AY 100023 and AY100022.

In addition, *M. vitigenus* 2116 is obtained as an endophyte from a liana growing in the upper Amazon (Daisy et al., 2002). Several small limbs of *P. paullinioides* were removed from a plant growing near Lake Sandoval in the Bahuaja Sonene Park Nacional in the extreme south of Peru, 12° 36' 27" N, 69° 01' 58" W.

The biologically pure culture can be in a variety of forms, including, but not limited to, still cultures, whole cultures, stored stocks of mycelium and/or hyphae (particularly glycerol stocks), stored agar plugs in glycerol/water, freeze dried stocks, and dried stocks such as mycelia dried onto filter paper. In addition, the cultures can be formulated using any number of carriers that confer a variety of properties, such as increased stability, wettability, dispersability, etc. Suitable formulations are known (wettable powders, granules, and the like, microencapsulated particles, liquids such as aqueous flowables, aqueous suspensions, etc.).

Agricultural carriers including soil are particularly preferred.

*M. vitigenus* can be identified by its ability to produce naphthalene, including naphthalene derivatives. By "naphthalene" herein is meant $C_{10}H_8$. As will be appreciated by those in the art, any of the carbon atoms on the two rings of naphthalene may be substituted by one or more R groups, independently selected from: halogens, alkyl (and ail its derivatives, including cycloalkyl, heteroalkyl, and substituted alkyl and heteroalkyl, wherein the substitution group is an "R" group), aryl (and all its derivatives, including heteroaryl and substituted aryl and heteroaryl), alcohol (including ethylene glycols), alkoxy, amino, amido, nitro, ethers, esters, aldehydes, sulfonyl, silicon moieties, halogens, sulfur containing moieties and phosphorus containing moieties. It should be noted that some positions may allow two substitution groups, R and R', in which case the R and R' groups may be either the same or different. In addition, R groups on adjacent carbons, or adjacent R groups, can be attached to form cycloalkyl or cycloaryl groups, including heterocycloalkyl and heterocycloaryl groups (and substituted derivatives thereof) together with the carbon atoms of the ring. These may be multi-ring structures as well. Particularly preferred naphthalene derivatives that may be produced by *M. vitigenus* are 2-methyl naphthalene, and 1-methoxy naphthalene as outlined in the examples. Other *M. vitigenus* isolates may have additional derivatives.

The *M. vitigenus* isolates of the present invention produce enough naphthalene to repel insects, for example as measured in the Y-tube tests outlined in the Examples. In general, MV isolates can be identified by the rate of naphthalene production using the system outlined in the examples, with rates from 5-150 ng $hr^{-1}$ being preferred, and rates in between and sometimes higher.

Also included within the definition of *M. vitigenus* species are variant strains. The "parent strain" is defined herein as a naturally occurring original *M. vitigenus* strain before mutagenesis. Parental strains can be mutagenized for a variety of reasons. This may involve doing classical or recombinant mutagenesis on the naturally occurring organism to develop strains that produce higher levels of one or more of the volatile compounds, or that produce different ratios of the volatile compounds. Additionally, mutagenesis may be done to alter the storage stability of the culture. Mutagenesis can include classical mutagenesis such as treatment with chemicals such as N-methyl-N'-nitro-N-nitrosoguanidine, ethylmethanesulfone or other classical mutagens, or by irradiation using gamma, x-ray or UV irradiation, or by other means well known in the art (see for example Sambrook text) for a variety of mutagenic techniques.

A "variant" is a strain having all the identifying characteristics of the strains of this invention and can be identified as having a genome that hybridizes under conditions of high stringency to the genome of the organism, the partial sequence of which has been deposited in the GenBank depository. "Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific mariner. The complex may comprise two strands forming a duplex structure, three or more strands forming a multi-stranded complex, a single self-hybridizing strand, or any combination of these. Hybridization reactions can be performed under conditions of different "stringency." In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. A variant may also be defined as a strain having a genomic sequence that is greater than 85%, more preferably greater than 90% or more preferably greater than 950% o sequence identity to the genome of *M. vitigenus*. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters.

In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/cei-bin/BLAST.

Additional isolates or subspecies of *M. vitigenus* can be isolated by use of the *M. vitigenus* species of the present invention as described herein. As reported previously, *Muscodor* does not bear fruiting structures under known conditions and each of them produce volatile biologically active compounds. The *M. vitigenus* of the present invention is the first *Muscodor* species to produce naphthalene in the gaseous phase, and is actually the first microbe to be shown to produce naphthalene. A preferred selection/isolation system is described in Strobel et al., 2001 and Worapong et al., 2002. The method generally are done by using *M. vitigenus*, as the source of selective gasses, in the presence of plant material suspected of supporting other gas producing endophytes. In general, in many cases other fungal relatives in the xylariales are not sensitive to *Muscodor* gasses, and thus can selectively eliminate all microbes except its relatives.

The isolated *M. vitigenus* species of the present invention finds use in a wide variety of applications, including, but not limited to, arthropod repellents and arthrocides, particularly insect repellents and insecticides, antimicrobials, anthelmintics and vermicides. The biologically pure culture can be used, or materials can be inoculated with the *M. vitigenus* cultures.

In a preferred embodiment, the *M. vitigenus* species find use as either arthropod repellents or arthrocides. Particularly preferred arthropods are insects, and thus a preferred embodiment utilizes the *M. vitigenus* species as an insect repellent or an insecticide. Insect repellency is generally measured by a significantly statistical change in amount of insects moving away from the source of *M. vitigenus*.

For example, *M. vitigenus* could be useful for treatment of soils infested with insects and/or other pests that would otherwise harm crop or other ornamental plants. In this case, the fungus, *M. vitigenus*, would be inoculated into the soil under conditions of being covered or sealed for several days, then the plants could be placed in the soil with some reasonable certainty that no infestation will follow. It is to be noted that *M. vitigenus* is not a fungal pathogen and that it is not toxic to plants. The treatment or inoculation of plants with *M. vitigenus* may allow the systemic growth of the fungus as a symbiotic or endophytic organism throughout the plant. In this case, the fungus may establish itself within the plant as a harmless endophyte and serve to preclude the eventual attack of the plant by otherwise harmful insects.

Thus, in a preferred embodiment, soil inoculated with *M. vitigenus* is used as the starting point. Other embodiments include topical administration of the isolate to the plants (including all plant parts), either in dry or solution form. Additional embodiments include inoculating the seeds of the plant with an *M. vitigenus* culture or solution.

In one embodiment, the insect repellent qualities of the novel *M. vitigenus* species outlined herein can be used in other medical and industrial applications where bioactivity is desired.

In one embodiment, the *M. vitigenus* organisms of the present invention find use in antimicrobial applications, although naphthalene is not as powerful an antimicrobial as it is an insect repellent.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Fungal Isolation and Storage

The culture of *M. vitigenus* used in this study was isolated as an endophyte from a liana growing in the upper Amazon (Daisy et al., 2002). Several small limbs of *P. paullinioides* were removed from a plant growing near Lake Sandoval in the Bahuaja Sonene Park Nacional in the extreme south of Peru, 12° 36' 27" N, 69° 01' 58" W. Small pieces of the inner tissues of the plant were placed in specially prepared Petri plates that were part of a selection system designed to specifically isolate endophytes related to the *Muscodor* spp. and/or other fungi that produce volatile antibiotics (Strobel et al., 2001). This selection system has been described previously and includes the use of the known *Muscodor* spp. isolates as selection tools (Worapong et al.; 2002). *M. vitigenus*, a sterile, gas-producing fungus, has been classified as a member of the genus *Muscodor* primarily due to the relatedness between its 18S rDNA sequences to previously known members of this group and to the similarity of its hyphae to other *Muscodor* spp. (FIG. 4-7) (Daisy et al., 2002). The fungus could best be stored after growth on sterile filter paper that had been placed on natural potato dextrose agar (PDAN). This agar was made with 10 g potato starch pellets (Basic American, Rexburg Id.), 15 g sucrose, 15 g agar, and distilled water up to 1 liter. The paper with mycelial growth was removed from the plates and dried under a laminar flow hood, cut into pieces, and stored at −70° C. The fungus remained viable for at least 8 months in this manner. *M. vitigenus* also remained viable, but to a lesser degree, when its mycelium was stored on PDAN plugs in glycerol/distilled water and stored at −70° C. *M. vitigenus* is stored in the Montana State University Mycological Culture Collection (MONT) as No. 2116.

Example 2

Gas Volatile Analyses

Figure 2:
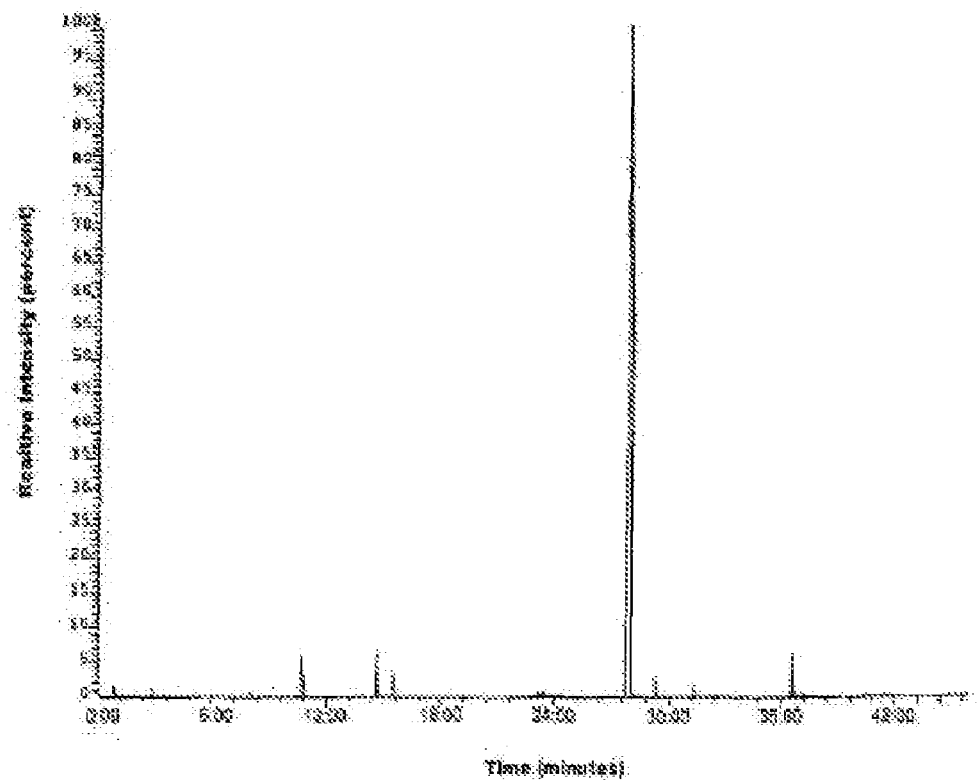
FIG. 2. The elution profile of volatiles trapped in the air space above a three-week-old colony of *M. vitigenus* and subjected to GC/MS. The major peak (28.03 min.) in this GS tracing has been identified as naphthalene.

The compounds produced as volatile secondary metabolites of a 21-day-old culture of *M. vitigenus* were initially identified by GC/MS. Comparable analyses (controls) were done on the gas phase trapped above an uninoculated PDAN Petri plate. Compounds appearing in the control plate were subtracted from the analyses of those trapped on the plate supporting fungal growth. Some of compounds in the control Petri plate were styrene, benzaldehyde, butylated hydroxytoluene, toluene, and a number of minor benzene derivatives including benzene, 1,3,5 trimethyl and benzene, 1-methoxy-3-methyl. Initial identification of the volatile compounds in both analyses was based on a comparison of the mass spectral data acquired after separation on by GC/MS with the NIST database. The most abundant compound appearing in the *M. vitigenus* culture atmosphere, based on the total integrated peak area of the GC elution profile, was naphthalene with a retention time of 28:03 min. (FIGS. 2 & 3). Final identification of the naphthalene was by comparison with an authentic standard (FIG. 3). The authentic standard had the same retention time and identical mass spectrum to that trapped in the atmosphere of the fungal culture. Several other naphthalene derivatives were also tentatively identified from the gas phase of *M. vitigenus* including traces of naphthalene, 2-methyl (30.24 min), and naphthalene, 1-methoxy (36:38 min). None of the other volatiles commonly associated with *M. albus* and *M. roseus* appeared in *M. vitigenus* except traces of acetone, caryoplylene, and azulene, 1,2,3,5,6,7,8,8a-octahydro-1,4-dimethyl-7-(-methylethenyl)-, [1S-(1.alpha.,7.alpha.,8a.beta.)] at 3:19, 24:18, and 37.12 min, respectively (Strobel et al., 2001).

Example 3

Rate of Naphthalene Release

Six plugs of PDAN (0.785 cm$^2$) supporting growth of 14 day-old *M. vitigenus* cultures were placed in a specialized volatile collection chamber, described previously, to find the rate of naphthalene released from each of them. Volatiles were collected for 3 hours and were then analyzed by GC/MS. Naphthalene identification was again confirmed as compared to an authentic standard and quantified using decane as an internal standard. The rate of naphthalene production, on six agar plugs, ranged from 9.45 ng hr$^{-1}$ to 106.85 hr$^{-1}$ with the mean production rate at 25.7±11.8.$^{-1}$ Although the range of naphthalene production is large, even the smallest yield of naphthalene proved to be great enough to modify insect behavior. Furthermore, on PDAN, naphthalene production began to occur at 7 days and continued for several weeks.

Example 4

Insect Repellancy Tests

Figure 1:
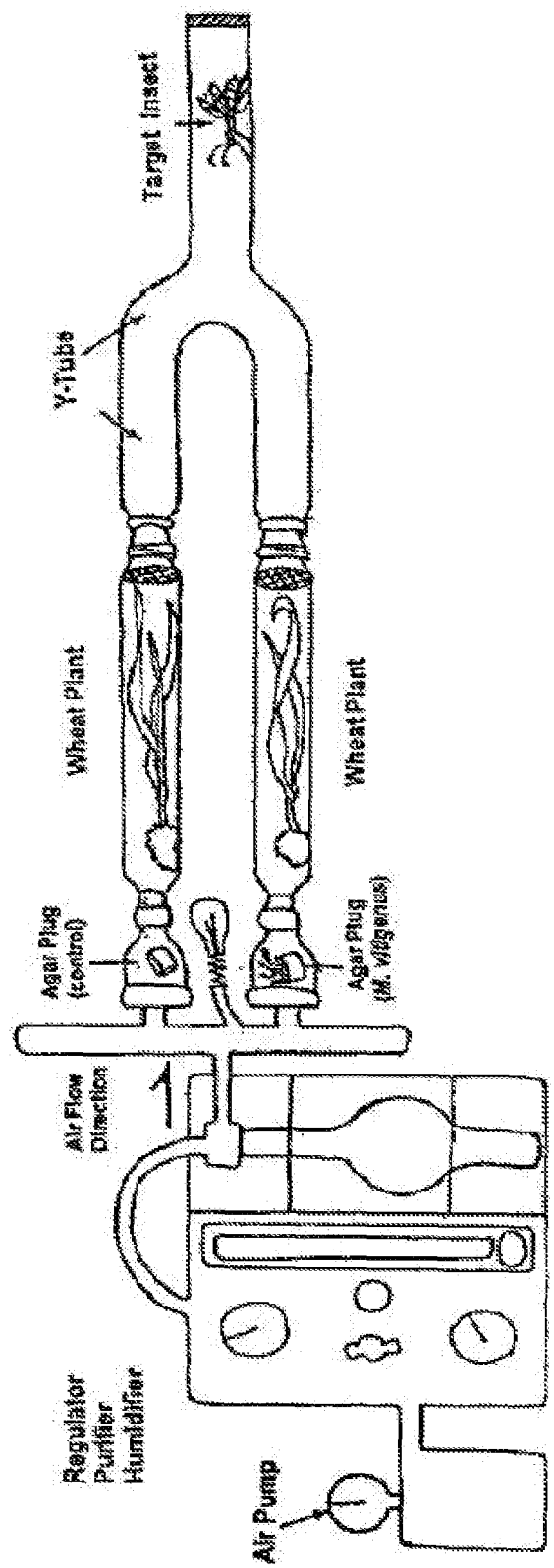
FIG. 1. A highly schematic drawing of the olfactory Y-tube used to measure insect behavior in the presence of various naphthalene sources. A 6.3 volt light source is placed at the base of the Y-tube as illustrated in the drawing.

In controlled, replicated experiments, both authentic naphthalene as well as *M. vitigenus*, were used as odor sources in Y-tube olfactometry tests (FIG. 1). The responses of *C. cinctus*, a major local crop pest, were measured with plugs of the naphthalene producing fungus as compared to comparable amounts of authentic naphthalene. Thirty successful trials using naphthalene test solution A (with a naphthalene release rate of 12 ng hr$^{-1}$) were completed (Table 1). Out of 30 insects, 24 responded by moving away from the naphthalene source. A second set of 30 successful trials were completed using naphthalene test solution B. Out of 30 insects, 21 were repelled by the naphthalene source. Finally, sixty successful trials were preformed using 0.0785 cm$^2$ fungal plugs (2-3 weeks old) of *M. vitigenus* as the odor source. Out of the 60 insects, 49 traveled away from the fungus and its volatiles. The results of both test concentrations of authentic naphthalene were statistically different from the acetone control test papers (Table 1). Insect behaviour in tests involving agar plugs containing *M. vitigenus* was also statistically different (a=0.001) from the controls (Table 1). Finally, many of the insects tested became more disoriented than usual in the presence of both commercial naphthalene as well as the *M. vitigenus* volatiles. Table 1. Influence of authentic naphthalene and *M. vitigenus* volatiles, containing mostly naphthalene, on the behavior of adult wheat stem sawflies (*C. cinctus*). Bioassay tests were conducted in Y-olfactory tubes.

| Test conditions* | Ratio: preference of insect to non-naphthalene side (control) of Y-tube vs. naphthalene source side of tube.* | Statistical evaluation Chi square test*** |
|---|---|---|
| Six PDAN plugs of a 2-week old *M. vitigenus* culture | 49/11<br>26 females, 34 males** | $X^2 = 22.81$<br>$\alpha = 0.001$ |
| Authentic naphthalene test concentration (A) | 24/6<br>15 females, 15 males | $X^2 = 9.63$<br>$\alpha = 0.005$ |
| Authentic naphthalene test concentration (B) | 21/9<br>15 females, 15 males | $X^2 = 4.03$<br>$\alpha = 0.05$ |

*The control side (numerator) of the Y-tubes, used in these tests, consisted of agar plugs (PDAN supporting no fungal growth) and in the case of authentic naphthalene-just an application of acetone containing no naphthalene to a paper disk as described. The denominator is the number of insects moving toward the naphthalene source.
**No differences were noted between male and female behavior.
***Statistical evaluation was performed on the differences in the behavior of insects in each test group between those moving toward the control side of the Y-tube to those moving toward the side containing naphthalene or *M. vitigenus*.

References

Agency for Toxic Substances and Disease Registry. (1995). World-Wide-Web Page at http://www.atsdr.cdc.gov/tfacts67.html.
Azuma, H., Toyota, M., Asakawa, Y., & Kawano, S. (1996). Naphthalene-constituent of magnolia flowers. Phytochemistry. 42: 999-1004.
Azevedo, J. L., Maccheroni, W., Jr., Pereira, J. O., and Araujo, W. L. 2000. Endophytic microorganisms: a review on insect control and recent advances on tropical plants. EJB Electronic Journal of Biotechnology. 3: Apr. 15, 2000.
Bacon, C. W. & White, J. F., Jr. 2000. Microbial Endophytes. New York: Marcel Dekker.
Bayman, P., Angulo-Sandoval, P., Baez-Ortiz, Z., and Lodge, D. J., 1997. Distribution and dispersal of Xylaria endophytes in two tree species in Puerto Rico. Mycological Research 102: 944-948.
Bolton, D. M., & Eaton, L. G. in the MERCK Index, 8$^{th}$ edn ed. (Stecher, P. G., Windholz, M., and Leahy, D. S.) 713 (MERCK, Rathway, N.J., 1968).
Bruns, T. D., White, T. J., and Taylor, J. W. 1991. Fungal molecular systematics. Annu. Rev. Ecol. Syst. 22: 525-564.
Chen, J., Henderson, G., Grimm, C. C., Lloyd S. W., & Laine, R. A. (1998). Termites fumigate their nests with naphthalene. Nature 392: 558-559.
Daisy, B. H., Strobel, G. A., Ezra, D., Castillo, U., Baird, G., & Hess, W. M., (2002).
*Muscodor vitigenus*, sp. nov. an endophyte from Paullinia. Mycotaxon 81.
Guarro, J., Gene, J., and Stchigel, A. M. 1999. Developments in Fungal Taxonomy. Clinical Microbiology Reviews. 12: 454-500.
Heath, R. R., & Manukian A. (1992). Development and evaluation of systems to collect volatile semiochemicals from insects and plants using a charcoal-infused medium for air purification. Journal of Chemical Ecology 18: 1209-1226.
Mitchell, J. I., Roberts, P. J., and Moss, S. T. 1995. Sequence or Structure? A Short Review on the Application of Nucleic Acid Sequence Information to Fungal Taxonomy. Mycologist. 9: 67-75.
Morrill, W. L., Weaver, D. K., & Johnson, G. D. (2001). Trap strip and field border modification for management of the wheat stem sawfly: (*Hymenoptera Cephidae*). Journal of Entomological Science 36: 34-45.
Pinkerton, F. & Strobel, G. A. (1976). Serinol as an activator of toxin production in attenuated cultures of *H. sacchari*. Proc. Natl. Aca. Sci. (USA) 73:4007-4011.
Reynolds, J., and Taylor, J. W. 1993. The Fungal Holomorph: Mitotic, Meiotic, and Pleomorphic Speciation in Fungal Systematics. Proceedings of an International Symposium Wallingford: C.A.B. International.
Sambrook, J., Fritsch, E. F., and Maniatis, T. 1989. Molecular Cloning: a Laboratory Manual, 2$^{nd}$ Edition. Edited by Ford, N., Nolan, C., and Ferguson, M. Cold Harbor Laboratory Press, New York. 1.74-1.84.
Sokal, R. R., & Rohlf, F., (1981). The Principles and Practice of Statistics in Biological Research. W. H. Freeman and Company, New York.
Stone, J. K., Bacon, C. W., & White, J. F. (2000). An overview of endophytic microbes endophytism defined in Microbial Endophytes ed. (Bacon, C. W., and White, J. F.), Marcel Decker, Inc, New York.
Strobel, G. A., Yang, X., Sears, J., Kramer, R., Sidhu, R. S., and Hess, W. M. 1996. Taxol from *Pestalotiopsis microspora*, an endophytic fungus of *Taxus walliachiana*. Microbiology. 142:435-440.
Strobel, G. A., Ford, E., Worapong, J., and Hess, W. M. 2000. *Pestalotiopsis jesteri* sp. nov. an endophyte from *Fragraea bodeni* from the southern highlands of Papua New Guinea. Mycotaxon. 76: 257-266.
Strobel, G. A., Dirske, E., Sears, and Markworth, C. 2001. Volatile antimicrobials from *Muscodor albus*, a novel endophytic fungus. Microbiology. 147: 2943-2950.
Taylor, J. W., Jacobsen, D. J., and Fisher, M. C. 1999. The Evolution of Asexual fungi: Reproduction, Speciation, and Classification. Annu. Rev. Phytopathol. 37: 197-246.
Weiland, J. J. http://www.fgsc.net/fgn44/weiland.html.
White, T. J., Bruns, T., and Taylor, J. W., 1990. Amplification of direct sequencing of fungal ribosomal RNA genes for phylogenetics. In PCR Protocols: A Guide to Methods and Applications. Edited by Innis, M. A., Gelfand, D. H., Sninsky J. J., and White, T. J. Academic Press, Inc., California: 315-324.
Worapong, J., Strobel, G. A., Ford, E., Li, J. Y., Baird, G., and Hess, W. M. 2001. *Muscodor albus* anam. gen. et sp. nov., an endophyte from *Cinnamomum zeylanicum*. Mycotaxon. 79: 67-79.

Worapong, J., Strobel, G. A., Daisy, B. H., Castillo, U., Baird, G., and Hess, W. M. 2002. *Muscodor roseus* sp. nov. an. endophyte from *Grevillea pteridifolia*. Mycotaxon. 81: 463-475.

Zadoks, J. C., Chang, T. T., & Konsak C. F. (1974). A decimal code for the growth stages of cereals. Weed Research 14: 15-21.

What is claimed is:

1. An isolated culture of *Muscodor vitigenus*, wherein the culture is *Muscodor vitigenus* 2116 (Accession No. CBS 120164) and is capable of producing a product comprising naphthalene.

2. A composition comprising the isolated culture of claim 1 and at least one carrier.

3. The composition of claim 2, wherein the carrier is an agriculturally acceptable carrier.

4. The composition of claim 3, wherein said carrier is soil.

5. The culture of claim 1, wherein the product further comprises 2-methyl naphthalene, 1-methoxy naphthalene or a combination thereof.

6. A method of repelling an insect from a first composition comprising contacting said first composition with a second composition comprising an isolated culture of *M. vitigenus* 2116 (Accession No. CBS 120164).

7. A method according to claim 6 wherein said first composition is a plant or a plant part.

8. A method according to claim 7 wherein said plant part is selected from the group consisting of seeds, fruits, stems, leaves and roots.

9. A method according to claim 7 or 8 wherein said second composition is soil inoculated with the isolated culture of *M. vitigenus* 2116 (Accession No. CBS 120164).

10. An isolated culture of *Muscodor vitigenus*, wherein the culture is *Muscodor vitigenus* 2116 (Accession No. CBS 120164) and is capable of producing naphthalene at a rate of about 5 ng $hr^{-1}$ to about 150 ng $hr^{-1}$.

11. The culture of claim 10, wherein the rate is about 5 ng $hr^{-1}$ to about 12 ng $hr^{-1}$.

* * * * *